United States Patent [19]

Willems et al.

[11] 4,013,473
[45] Mar. 22, 1977

[54] RECORDING MATERIALS AND IMAGE RECEIVING MATERIALS FOR PRODUCING COPIES IN A DRY WAY

[75] Inventors: Jozef Frans Willems, Wilrijk; Albert Lucien Poot, Kontich; Jan Frans Van Besauw, Mortsel, all of Belgium; Alfons Klein, Dusseldorf; Karlfried Wedemeyer, Cologne-Stammheim, both of Germany

[73] Assignee: AGFA-GEVAERT N.V., Mortsel, Belgium

[22] Filed: Aug. 21, 1975

[21] Appl. No.: 606,489

[30] Foreign Application Priority Data

Aug. 24, 1974   Germany ........................ 2440678

[52] U.S. Cl. ........................ 96/114.1; 96/27 R; 96/48 HD; 96/66 T; 250/317; 427/145; 428/411; 428/913

[51] Int. Cl.² ...................... G03C 1/42; G03C 5/30

[58] Field of Search .................... 427/144–146; 250/316–318; 96/27 R, 28, 48 HD, 114.1, 66 R, 66 T; 428/913, 411

[56] References Cited

UNITED STATES PATENTS

| | | | |
|---|---|---|---|
| 2,910,377 | 10/1959 | Owen .......................... | 428/913 X |
| 3,074,809 | 1/1963 | Owen .......................... | 428/913 X |
| 3,080,254 | 3/1963 | Grant .......................... | 250/317 X |
| 3,107,174 | 10/1963 | Wartman ..................... | 250/317 X |
| 3,186,843 | 6/1965 | Haas ........................... | 96/66 R |
| 3,218,166 | 11/1965 | Reitter ........................ | 96/27 R |
| 3,547,648 | 12/1970 | Sagawa ....................... | 96/67 |
| 3,615,533 | 10/1971 | Rauner et al. ................ | 250/316 X |
| 3,751,252 | 8/1973 | Smith et al. .................. | 250/316 X |
| 3,941,596 | 3/1976 | Heiart .......................... | 96/28 |
| 3,965,282 | 6/1976 | Janssens et al. .............. | 250/317 X |

*Primary Examiner*—Harold Ansher
*Attorney, Agent, or Firm*—William J. Daniel

[57] ABSTRACT

Thermographic recording material or image-receiving material for dry copying processes comprising at least one layer and a substantially non-photosensitive reducible silver salt, a reducing agent, and optionally a toning agent or toning mixture, wherein the reducing agent corresponds to the following general formula:

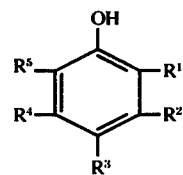

wherein:
each of $R^1$, $R^3$ and $R^5$ (equal or different) represents hydrogen, a straight-chain or branched alkyl group comprising 1 to 9 carbon atoms, or a cycloalkyl group, with the proviso that $R^1$ and $R^5$ do not represent hydrogen simultaneously, $R^2$ represents a straight-chain or branched alkyl group comprising 1 to 4 carbon atoms, or a cycloalkyl group, $R^4$ represents hydrogen, or a straight-chain or branched alkyl group comprising 1 to 4 carbon atoms, or a cycloalkyl group, and wherein each of $R^1$ and $R^2$ together, $R^2$ and $R^3$ together or $R^4$ and $R^5$ together optionally represent a straight-chain or branched alkylene group for completing a 6-membered ring; provided that that $R^1$, $R^5$ or $R^3$ does not represent t-butyl if the respective adjacent substituent(s) represent(s) a straight-chain or branched alkyl group.

13 Claims, No Drawings

RECORDING MATERIALS AND IMAGE RECEIVING MATERIALS FOR PRODUCING COPIES IN A DRY WAY

This invention relates to improved recording materials and image-receiving materials for dry processes of producing copies of graphic originals and to the use of such materials in thermal recording processes and photographic processes.

Dry thermal recording and photographic processes for producing copies of an original are already known. The materials used for these processes contain light-sensitive or heat-sensitive layers. When these layers are exposed image-wise to light or heat, a colour-producing reaction is initiated, which results in the formation of an image.

Heat-sensitive copying sheets that change colour imagewise by a thermally initiated reduction reaction have been disclosed in U.K. Patent No. 866,076, filed June 28, 1957 by Minnesota Mining and Manufacturing Co. As image-forming reagents non-light-sensitive silver salts, e.g. silver behenate, and 2,3-dihydroxybenzoic acid have been proposed. According to the process described therein heat-sensitive copying sheets, which are capable of image-wise absorbing infrared radiation, are used for the thermographic copying of originals. For this purpose the original is exposed to infrared radiation in thermoconductive contact with such copying sheet. The infrared-absorbing image portions of the original are selectively heated and by heat transfer cause the development in the adjacent heat-sensitive sheet of a silver image corresponding with the image markings of the original.

Other methods of producing copies by image-wise exposure of a light-sensitive layer are known in which the layer contains a light-sensitive compound and an image-producing compound which is transferrable to an image-receiving layer. In these processes, the image-producing compound is converted in the light-struck areas into a non-transferrable compound, the exposed layer is brought into contact with an image-receiving layer, which contains compounds capable of reacting with the image-producing compound to form coloured compounds, whereupon both layers are heated in contact with each other to a temperature at which the image-producing compound is transferred from those areas of the light-sensitive layer which have not been struck by light to the image-receiving layer.

This type of copying process includes the process described in German Patent No. 1,234,243 filed Jan. 2, 1962 by Minnesota Mining and Manufacturing Co., in which the light-sensitive layers used contain a volatile compound and a dye. Exposure to light converts the volatile compound, e.g. 4-methoxy-1-naphthol, into a non-volatile product. By a subsequent heating of the layer this compound can be transferred from the areas that have not been struck by light to a receiving material where it reacts with a silver salt to produce a coloured positive image.

A similar process has been described in U.S. Pat. No. 3,094,417 of Wesley R. Workman issued June 18, 1963, U.S. Pat. No. 3,619,237 of Albert W. Leclair issued Nov. 9, 1971 and in French Patent No. 2,037,847 filed Mar. 9, 1970 by Nashua Corporation, in which acetoacetonitrile derivatives or pyrazolin-5-one derivatives, which can be inactivated by light, transferred by heat and react with a silver salt, are used.

The receiving sheet preferably contains a non-light-sensitive silver salt of a long-chain fatty acid as image-producing substance as well as a so-called auxiliary reducing agent. For this purpose have been proposed the weak reducing agents such as o-alkyl-substituted phenols or hydroxycoumarans and hydroxychromans described, e.g., in the published German Patent Applications (DOS) Nos. 1,908,761 filed Feb. 18, 1969 by Minnesota Mining and Manufacturing Co. and 2,031,748 filed June 26, 1970 by Agfa-Gevaert AG or in German Patent No. 1,250,842 filed Nov. 21, 1963 by Minnesota Mining and Manufacturing Co.

In U.S. Pat. No. 3,218,166 of John L. Reitter issued Nov. 16, 1965, a receiving material for these copying processes has been described, which contains a silver salt of a fatty acid, a toning agent for achieving black silver images and a bis-t-alkylphenol as auxiliary reducing agent.

According to U.S. Pat. No. 3,547,648 of Burt K. Sagawa issued Dec. 15, 1970, a t-alkylmonophenol mixed with a di-t-alkylbisphenol is used in the above copying processes for improving the density and the contrast of the images.

In the prior art layers incorporating silver salts of the thermographic recording and image-receiving layers the quantity of reducing agent must be kept to a minimum in order to prevent unwanted darkening of the casting solution or of the layer, i.e., reduction of the organic silver salts during preparation and storage of the material.

Apart from the fact that some of the known materials have insufficient stability during preparation and storage, there is the further disadvantage that discolouration is found to take place in the background of the image, i.e., in the image whites, due to oxidation of the reducing agents which remain in the layer after its preparation. In some of the known reducing agents this discolouration is so severe that a yellow or brown patchy background is formed after only a short time in storage.

It is an object of this invention to find reducing agents for the photographic processes described above which will not reduce the stability of the material during preparation or storage and will have no deleterious effect on the whites of the finished photographic image.

A thermographic recording material or image-receiving material for dry copying processes has now been found which comprises at least one layer and a substantially non-photosensitive reducible silver salt, a reducing agent, and optionally a toning agent or toning mixture, wherein the reducing agent corresponds to the following general formula

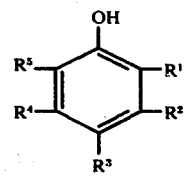

wherein:
    each of $R^1$, $R^3$ and $R^5$ (equal or different) represents hydrogen, a straight-chain or branched alkyl group comprising 1 to 9 carbon atoms, e.g. isopropyl, s-butyl, t-butyl, iso-octyl or isononyl, or a cycloalkyl group, e.g. cyclopentyl or cyclohexyl, with the proviso that $R^1$ and $R^5$ do not represent hydrogen simultaneously, $R^4$ represents hydrogen, or a straight-chain or branched alkyl group comprising 1 to 4 carbon atoms, e.g. methyl, isopropyl or t-butyl, or a cycloalkyl group, e.g. cyclopentyl or cyclohexyl, $R^2$ represents a straight-chain or branched alkyl group comprising 1 to 4 carbon atoms, e.g. methyl or t-butyl, or a cycloalkyl group, e.g. cyclopentyl or cyclohexyl, and wherein each of $R^1$ and $R^2$ together, $R^2$ and $R^3$ together or $R^4$ and $R^5$ together optionally represent a straight-chain or branched alkylene group for completing a 6-membered ring, with the proviso that $R^1$, $R^5$ or $R^3$ does not represent t-butyl, if the respective adjacent substituent(s) represent(s) a straight-chain or branched alkyl group.

Especially suited are the phenols of the above formula wherein $R^1$, $R^2$, $R^3$, $R^4$ and $R^5$ are substituents listed in the following table I.

to 212° C at 1.4 mm Hg which are recrystallised from ligroin. Yield: 143 g of 2,4,5-tricyclopentylphenol. Melting point: 104° C.

COMPOUND 2

In an autoclave 222 g of 2-hydroxytetraline, 2.5 g of aluminium grit and 0.2 g of mercury(II) chloride are heated at 180° C for 1 h. After cooling 85 g of isobutylene are added and the mixture is stirred at 100° C for 3 h. In order to eliminate the catalyst the reaction product is washed with diluted hydrochloric acid. A subsequent distillation yields 212 g of 1-t-butyl-2-hydroxytetraline. Boiling point (13 mm Hg): 171° C. Melting point: 104° C.

COMPOUNDS 3 AND 4

To 122 g of 3,4-dimethylphenol and 12.2 g of p-toluene sulphonic acid 150 g of cyclopentene are added dropwise at 120° C whereupon the mixture is stirred at this temperature for 6 h. The reaction product obtained

TABLE I

| Number | $R^1$ | $R^2$ | $R^3$ | $R^4$ | $R^5$ |
|---|---|---|---|---|---|
| 1 | H | cyclopentyl | cyclopentyl | H | cyclopentyl |
| 2 | t-butyl | —CH$_2$—CH$_2$— | CH$_2$—CH$_2$— | H | H |
| 3 | H | CH$_3$ | CH$_3$ | H | cyclopentyl |
| 4 | cyclopentyl | CH$_3$ | CH$_3$ | H | cyclopentyl |
| 5 | cyclopentyl | —CH$_2$—CH$_2$— | CH$_2$—CH$_2$— | H | cyclopentyl |
| 6 | H | cyclopentyl | CH$_3$ | H | cyclopentyl |
| 7 | H | CH$_3$ | cyclopentyl | H | cyclopentyl |
| 8 | H | cyclopentyl | CH$_3$ | H | CH$_3$ |
| 9 | —CH(CH$_3$)CH$_2$CH$_3$ | CH$_3$ | —CH(CH$_3$)CH$_2$CH$_3$ | H | H |
| 10 | H | CH$_3$ | —CH(CH$_3$)CH$_2$CH$_3$ | H | —CH(CH$_3$)CH$_2$CH$_3$ |
| 11 | H | CH$_3$ | H | H | cyclopentyl |
| 12 | H | t-butyl | H | H | —CH(CH$_3$)CH$_2$CH$_3$ |
| 13 | H | cyclopentyl | H | H | t-butyl |
| 14 | H | —CH(CH$_3$)CH$_2$CH$_3$ | CH$_3$ | H | —CH(CH$_3$)CH$_2$CH$_3$ |
| 15 | CH$_3$ | isopropyl | H | H | CH$_3$ |
| 16 | H | t-butyl | H | H | t-butyl |
| 17 | H | CH$_3$ | CH$_3$ | H | t-butyl |
| 18 | H | CH$_3$ | CH$_3$ | H | cyclohexyl |
| 19 | H | CH$_3$ | H | H | t-butyl |
| 20 | H | CH$_3$ | t-butyl | H | t-butyl |
| 21 | H | CH$_3$ | CH$_3$CH$_2$ | H | CH$_3$ |
| 22 | H | CH$_3$ | CH$_3$CH$_2$ | H | t-butyl |
| 23 | cyclohexyl | CH$_3$ | CH$_3$ | H | cyclohexyl |
| 24 | isopropyl | CH$_3$ | CH$_3$ | isopropyl | H |
| 25 | isopropyl | CH$_3$ | H | CH$_3$ | isopropyl |
| 26 | isopropyl | CH$_3$ | isopropyl | H | isopropyl |
| 27 | —CH$_2$—CH$_2$— | CH$_2$—CH$_2$— | cyclopentyl | H | cyclopentyl |
| 28 | isopropyl | CH$_3$ | H | CH$_3$ | H |
| 29 | —CH$_2$—OH$_2$— | CH$_2$—CH$_2$— | isopropyl | H | isopropyl |
| 30 | —CH$_2$—CH$_2$— | CH$_2$—CH$_2$— | H | H | cyclopentyl |
| 31 | cyclopentyl | CH$_3$ | H | CH$_3$ | H |
| 32 | cyclopentyl | CH$_3$ | H | CH$_3$ | cyclopentyl |
| 33 | isopropyl | CH$_3$ | CH$_3$ | H | isopropyl |
| 34 | cyclopentyl | CH$_3$ | cyclopentyl | H | cyclopentyl |
| 35 | cyclohexyl | CH$_3$ | H | CH$_3$ | cyclohexyl |
| 36 | cyclopentyl | CH$_3$ | H | isopropyl | cyclopentyl |
| 37 | cyclopentyl | CH$_3$ | H | H | isopropyl |
| 38 | cyclohexyl | CH$_3$ | H | isopropyl | cyclohexyl |
| 39 | isopropyl | CH$_3$ | H | H | isopropyl |
| 40 | cyclopentyl | CH$_3$ | cyclopentyl | H | isopropyl |
| 41 | cyclopentyl | CH$_3$ | H | H | cyclopentyl |
| 42 | isopropyl | CH$_3$ | H | isopropyl | isopropyl |
| 43 | s-butyl | CH$_3$ | H | H | s-butyl |
| 44 | cyclohexyl | CH$_3$ | H | H | cyclohexyl |

The preparation of the compounds listed in table I is detailedly described hereinafter.

COMPOUND 1

To 470 g of phenol and 100 g of an acid-activated fuller's earth 1020 g of cyclopentene are added dropwise at 140° C whereupon the mixture is stirred at the same temperature for 15 h. After elimination of the catalyst by filtration the reaction mixture is distilled by fractionation. Besides 2,4,6-tricyclopentylphenol 173 g of a fraction are obtained having a boiling range of 205° is freed from the catalyst by washing with water and sodium hydrogen carbonate solution and fractionated. Yield: 30 g 3,4-dimethyl-6-cyclopentylphenol. Boiling point (1.1 mm Hg): 121° C. The residue of this distillation is recrystallised from isooctane. Yield: 102 g of 3,4-dimethyl-2,6-dicyclopentylphenol. Melting point: 62° C.

COMPOUND 5

375 g of cyclopentene are added dropwise to 370 g of 2-hydroxytetraline and 37.5 g of toluene sulphonic acid at 120° C. The mixture is stirred at 120° for further 3 h. The catalyst is removed by washing with water and sodium hydrogen carbonate solution. The forerunnings distilling through a laboratory column of 1 m filled with packing material until a boiling point of 196° C (0.9 mm Hg) are discarded. The residue is then distilled without column. This distillate is recrystallised from petroleum ether. Yield: 207 g of dicyclopentyl-2-hydroxytetraline. Melting point: 71° C.

COMPOUND 6

840 g of cyclopentene are added dropwise to 648 g of p-cresol and 60 g of an acid-activated fuller's earth at 140° C. Next the mixture is stirred at 140° C for 15 h. After having removed the catalyst by filtration the mixture is fractionated. In the boiling range of 153°–156° C 540 g of 2,6-dicyclopentyl-4-methylphenol are obtained (0.8 mm Hg) and between 167°–170° C 422 g of a fraction (0.8 mm Hg) which is recrystallised from petroleum ether. Yield: 360 g of 2,5-dicyclopentyl-4-methylphenol. Melting point: 78° C.

COMPOUNDS 11 AND 7

130 g of cyclopentene are added dropwise to 108 g of m-cresol and 10 g of an acid-activated fuller's earth at 140° C. The mixture is stirred at this temperature for 1 h. After removal of the catalyst by filtration the mixture is fractionated. 35 g of 3-methyl-6-cyclopentylphenol boiling at 113° C (1.4 mm Hg) are obtained. A further fraction (112 g) boiling at 154° C (0.9 mm Hg) consists of 3-methyl-4,6-dicyclopentylphenol (melting point: 45° C).

COMPOUND 8

76 g of cyclopentene are added dropwise to 122 g of 2,4-dimethylphenol and 10 g of an acid-activated fuller's earth at 140° C. This mixture is stirred at this temperature for 3 h. After removal of the catalyst by filtration it is fractionated. A first fraction boiling between 102° and 105° C (0.6 mm Hg) consists of 95 g of 2,4-dimethyl-6-cyclopentylphenol and a second fraction boiling between 115° and 119° C (0.5 mm Hg) consists of 60 g of a product, which is recrystallised from petroleum ether. Yield: 45 g of 2,4-dimethyl-5-cyclopentylphenol. Melting point: 84° C.

COMPOUNDS 9 AND 10

162 g of m-cresol and 16 g of an acid-activated fuller's earth are placed in an autoclave to which 168 g of butane-1 are pumped at 110° C. The mixture is allowed to react at this temperature for 5 h. After removal of the catalyst by filtration the mixture is fractionated. At the boiling points of 140° C (12 mm Hg) and 158° C (12 mm Hg) 33 g of 3-methyl-2,4-di-s-butylphenol and 165 g of 3-methyl-4,6-di-s-butylphenol are obtained respectively.

COMPOUND 12

48 g of isobutylene are introduced at 110° C in 150 g of 2-s-butylphenol and 6 g of an acid-activated fuller's earth. The mixture is allowed to react at this temperature for 16 h. After removal of the catalyst by filtration the mixture is fractionated and the following products are obtained besides non-reacted 2-s-butylphenol:
1. 81 g of 2-s-butyl-4-t-butylphenol. Boiling point (12 mm Hg): 139° C
2. 59 g of 2-s-butyl-5-t-butylphenol. Boiling point (12 mm Hg): 147° C. Melting point: 41° C.

COMPOUND 13

230 g of isobutylene are introduced at 80° C in a mixture of 324 g of 3- and 4-cyclopentylphenol (70:30) and 40 g of an acid-activated fuller's earth. The mixture is stirred at 130° C for 5 h and is fractionated after removal of the catalyst by filtration. Yield: 103 g of 3-cyclopentyl-6-t-butylphenol boiling at 180° C (12 mm Hg).

COMPOUND 14

230 g of butene-1 are introduced in 216 g of p-cresol and 20 g of an acid-activated fuller's earth at 140° C. The mixture is allowed to react at this temperature for 4 h. After removal of the catalyst by filtration the mixture is fractionated. Yield: 164 g of 4-methyl-2,6-di-s-butylphenol boiling at 102° C (0.7 mm Hg) and 107 g of 4-methyl-2,5-di-s-butylphenol boiling at 112° C (0.7 mm Hg).

COMPOUND 15

87 g of propylene are introduced at 100° C in 244 g of 2,6-dimethylphenol and 10 g of an acid-activated fuller's earth. The mixture is stirred at this temperature for 4 h whereupon the catalyst is removed by filtration. The mixture is fractionated and in the boiling range of 120°–135° C (12 mm Hg) a fraction is collected, which is recrystallised from petroleum ether. Yield: 16 g of 2,6-dimethyl-3-isopropylphenol. Melting point: 44° C.

COMPOUNDS 16 TO 20

These compounds are prepared as described in J. Am. Chem. Soc. 69 (1947) 2086, Rec. Inst. Franc. Petrole 15 (1960) 680–697, French Patent 1,315,008 filed January 9, 1959 by institut Francais des Petroles, des Carburants et Lubrifiants, U.S. Pat. No. 2,784,239 by Andrew J. Dietzler and Fred Bryner, issued Mar. 5, 1957 and Belgian Patent 622,404 filed Sept. 12, 1962 by Rutges Werke A.G., respectively.

COMPOUND 21

In an autoclave 100 g of 1,1-bis(2,5-dimethyl-4-hydroxyphenyl)-ethane, 100 g of cyclohexanol and 5 g of catalyst (5% palladium on charcoal) are stirred at 270° C for 7 h. Thereupon the catalyst is removed by filtration and the reaction product is fractionated. As forerunnings cyclohexanone and 2,5-dimethylphenol are obtained. At boiling point 124° C (12 mm Hg) 33 g of pure 2,5-dimethyl-4-ethylphenol are obtained.

COMPOUND 22

In an autoclave are placed 100 g of 1,1-bis(2-methyl-5-t-butyl-4-hydroxyphenyl)-ethane, 100 g of cyclohexanol and 5 g of a catalyst consisting of 5% of palladium precipitated on charcoal. The contents are stirred at 230° C for 8 h. After removal of the catalyst by filtration the mixture is fractionated. As forerunnings cyclohexanone and 3-methyl-6-t-butylphenol are obtained. At boiling point 143° C (14 mm Hg) 39 g of 3-methyl-4-ethyl-6-t-butylphenol are collected.

COMPOUND 23

170 g of cyclohexene are added dropwise at 80° C to 122 g of 3,4-dimethylphenol and 12 ml of boron fluoride etherate. This mixture is then stirred at that temperature for 2 h. The reaction product is dissolved while warm in toluene and washed with water in order to remove the catalyst. On cooling crystals precipitate, which are recrystallised from iso-octane. Yield: 106 g. Melting point: 98° C.

COMPOUND 24

90 g of propylene are introduced to 122 g of 3,4-dimethylphenol and 12 ml of boron fluoride etherate at 110° C. The reaction mixture is then stirred at this temperature for 2 h. The catalyst is removed by washing with water and the reaction product is then fractionated. The forerunnings contain 3,4-dimethyl-2,6-diisopropylphenol. In the boiling range 150°–165° C (12 mm Hg) a fraction is obtained which is recrystallised from petroleum ether. Yield: 30 g of 3,4-dimethyl-2,5-diisopropylphenol. Melting point: 87° C.

COMPOUND 25

86 g of propylene are introduced in 122 g of 3,5-dimethylphenol and 12 g of an acid-activated fuller's earth at 120° C. The mixture is then stirred at this temperature for 2 h. The reaction product is taken up in toluene and freed from the catalyst by filtration. After evaporation of the solvent a crystal slurry is obtained, which is recrystallised from methanol. Yield: 81 g of 3,5-dimethyl-2,6-diisopropylphenol. Melting point: 95° C.

COMPOUND 26

260 g of propylene are introduced into 216 g of m-cresol and 22 ml of boron fluoride etherate at 80° C. The mixture is then stirred at this temperature for 2 h. After filtration of the catalyst and fractionation 194 g of 3-methyl-2,4,6-triisopropylphenol are collected at boiling point 149° C (12 mm Hg).

COMPOUND 27

140 g of cyclopentene are added dropwise to 148 g of 1-hydroxytetraline and 12 ml of boron fluoride etherate. The mixture is then stirred at this temperature for 3 h. The catalyst is removed by washing with water. Thereupon the reaction mixture is fractionated. The fraction boiling between 183° and 190° C (0.7 mm Hg) is recrystallised from petroleum ether. Yield: 91 g of 1-hydroxy-2,4-dicyclopentyltetraline.

COMPOUND 28

63 g of propylene are introduced into 244 g of 3,5-dimethylphenol and 22 g of p-toluene sulphonic acid at 120° C. Thereupon the mixture is stirred at this temperature for 3 h. The catalyst is removed by washing with sodium hydrogen carbonate solution. Then the mixture is fractionated. At boiling point 120° C (12 mm Hg) 57 g of 3,5-dimethyl-2-isopropylphenol are obtained.

COMPOUND 29

85 g of propylene are introduced into 148 g of 1-hydroxytetraline and 12 ml of boron fluoride etherate at 80° C. The mixture is then stirred at this temperature for 3 h. The catalyst is removed by washing with water. Then the mixture is fractionated. At boiling point 181° C (12 mm Hg) 53 g of 1-hydroxy-2,4-diisopropyltetraline are obtained.

COMPOUND 30

40 g of cyclopentene are added dropwise at 120° C to 148 g of 1-hydroxytetraline and 10 g of p-toluene sulphonic acid. The catalyst is removed by washing with sodium hydrogen carbonate solution. The reaction mixture is fractionated. At 161° C (2 mm Hg) 58 g of 1-hydroxy-2-cyclopentyltetraline are obtained.

COMPOUND 31

102 g of cyclopentene are added dropwise to 244 g of 3,5-dimethylphenol and 20 g of p-toluene sulphonic acid at 120° C. The mixture is then stirred at this temperature for 2 h. After removal of the catalyst by washing with sodium hydrogen carbonate solution the mixture is fractionated. At boiling point 104° C (0.5 mm Hg) 90 g of 3,5-dimethyl-2-cyclopentylphenol are obtained.

COMPOUND 32

700 g of cyclopentene are added dropwise to 610 g of 3,5-dimethylphenol and 60 g of p-toluene sulphonic acid at 120° C. The catalyst is removed by washing with sodium hydrogen carbonate solution. The mixture is fractionated. At boiling point 141° C (0.6 mm Hg) 591 g of 3,5-dimethyl-2,6-dicyclopentylphenol are obtained. Melting point: 69° C.

COMPOUND 33

90 g of propylene are introduced into 122 g of 3,4-dimethylphenol and 12 ml of boron fluoride etherate at 110° C. The mixture is then stirred at this temperature for 2 h. The catalyst is removed by washing with water. Then the mixture is fractionated. At boiling point 142° C (12 mm Hg) 91 g of 3,4-dimethyl-2,6-diisopropylphenol are obtained.

COMPOUND 34

410 g of cyclopentene are added dropwise to 216 g of m-cresol and 22 ml of boron fluoride etherate at 80° C. The reaction mixture is then stirred at this temperature for 2 h. Then the catalyst is removed by washing with water and the reaction mixture is fractionated. At boiling point 195° C (1.0 mm Hg) 252 g of 3-methyl-2,4,6-tricyclopentylphenol are obtained.

COMPOUND 35

170 g of cyclohexene are added dropwise to a mixture of 122 g of 3,5-dimethylphenol and 12 ml of boron fluoride etherate with stirring at 80° C within 2 h. The mixture is stirred at this temperature for another 2 h whereupon the reaction product is dissolved in toluene and washed with aqueous sodium hydrogen carbonate solution. The cooled product freed from toluene is recrystallised from methanol. Yield: 177 g of 2,6-dicyclohexyl-3,5-dimethylphenol. Melting point: 118° C.

COMPOUND 36

136 g of cyclopentene are added dropwise to 150 g of 3-methyl-5-isopropylphenol and 15 g of p-toluene sulphonic acid at 120° C. The reaction mixture is then stirred at this temperature for 4 h. After removal of the catalyst by washing with aqueous sodium hydrogen carbonate solution the mixture is fractionated. In the boiling range 148°–150° C (0.2 mm Hg) 104 g of 3-methyl-5-isopropyl-2,6-dicyclopentylphenol are collected.

COMPOUND 37

136 g of cyclopentene are added dropwise to 600 g of 3-methyl-6-isopropylphenol and 30 g of p-toluene sulphonic acid at 100° C. The mixture is then stirred at this temperature for 2 h. The catalyst is removed by washing with aqueous sodium hydrogen carbonate solution. The mixture is then fractionated. In the boiling range 166°–168° C (12 mm Hg) 198 g of 3-methyl-2-cyclopentyl-6-isopropylphenol are collected.

COMPOUND 38

170 g of cyclohexene are added dropwise to 150 g of 3-methyl-5-isopropylphenol and 12 ml of boron fluoride etherate at 80° C. The mixture is then stirred at this temperature for 2 h. After removal of the catalyst by washing with aqueous sodium hydrogen carbonate solution the mixture is recrystallised from iso-octane. Yield: 89.5 g of 3-methyl-5-isopropyl-2,6-dicyclohexylphenol. Melting point: 123° C.

COMPOUND 39

45 g of propylene are introduced in 300 g of 3-methyl-6-isopropylphenol and 15 g of toluene sulphonic acid at 100° C. The mixture is then stirred at this temperature for 3 h. After removal of the catalyst by washing with aqueous sodium hydrogen carbonate solution the mixture is fractionated. In the boiling range 130°–132° C (12 mm Hg) 74 g of 3-methyl-2,6-diisopropylphenol are collected.

COMPOUND 40

172 g of cyclopentene are added dropwise to 300 g of 3-methyl-6-isopropylphenol and 20 ml of boron fluoride etherate at 80° C. The mixture is then stirred at this temperature for 5 h. After removal of the catalyst by washing with aqueous sodium hydrogen carbonate solution the mixture is fractionated. In the boiling range 175°–177° C (1.0 mm Hg) 94 g of 3-methyl-2,4-dicyclopentyl-6-isopropylphenol are collected.

COMPOUND 41

In an autoclave 216 g of m-cresol, 2.1 g of aluminium grit and 0.1 g of mercury(II) chloride are heated at 200° C for 1 h. After cooling at room temperature 272 g of cyclopentene are introduced whereupon the mixture is stirred at 200° C for 10 h. After the addition of 10 ml of 10% aqueous sodium hydroxide solution the reaction mixture is fractionated through a 1 m laboratory packed column. In the boiling range of 153°–155° C (0.9 mm Hg) 202.6 g of 2,6-dicyclopentyl-3-methylphenol are collected.

COMPOUND 42

130 g of propylene are introduced into 216 g of 3-methyl-5-isopropylphenol and 20 g of boron fluoride etherate at 80° C. The catalyst is removed by washing with aqueous sodium hydrogen carbonate solution. The reaction mixture is then fractionated. In the boiling range of 148°–150° C (12 mm Hg) 211 g of 3-methyl-2,4,6-triisopropylphenol are collected.

COMPOUND 43

In an autoclave 162 g of m-cresol, 1.6 g of aluminium grit and 0.1 g of mercury(II) chloride are heated at 200° C for 1 h. After cooling at room temperature 168 g of n-butene are added. This mixture is stirred at 200° C for 10 h. Then 10 g of 10% aqueous sodium hyroxide solution are added and the mixture is fractionated. At 142° C (12 mm Hg) 43.9 g of 3-methyl-2,6-di-s-butylphenol are obtained.

COMPOUND 44

In an autoclave 144 g of m-cresol, 2.9 g of aluminium grit and 0.1 g of mercury(II) chloride are heated at 100° C for 1 h. After cooling at room temperature 219 g of cyclohexene are added. This mixture is stirred at 200° C for 10 h. After the addition of 10 g of 10% aqueous sodium hydroxide solution the mixture is fractionated. Between 168 and 169° C (0.9 mm Hg) 51 g of 3-methyl-2,6-dicyclohexylphenol are collected.

The present invention comprises heat-sensitive recording materials as well as non-light-sensitive image-receiving materials for the preparation of photographic copies according to a dry transfer process, wherein the image-receiving layer contains substantially non-light-sensitive, reducible silver salts, a phenol derivative of the above formula as reducing agent and optionally a toning agent.

The materials according to the present invention can be prepared without difficulties. The coating solutions for the layers as well as the finished material possess outstanding keeping qualities. The special advantage is the quality of the finished images. Outstanding whites are obtained without any yellowing.

The thermographic recording and image-receiving materials containing phenol derivatives according to the present invention are used for the above described processes for the dry preparation of silver images.

The materials according to the invention may be used, e.g. in thermographic processes requiring a material with a layer which contains a non-photosensitive silver salt and a phenol derivative as reducing agent to reduce the silver salt in the heated areas. A process of this kind and materials for carrying it out have been described in U.S. Pat. No. 2,910,377 of Richard Owen issued Oct. 27, 1959.

The photographic materials according to the invention are also suited for being used in the transfer process described above for making positive copies by a dry process. The materials used in this process for producing positive copies are photosensitive materials comprising a layer that contains a photo-oxidizable reducing agent, which is transferrable at temperatures of between 80° and 200° C and a photosensitive substance that activates the oxygen (to the triplet state) in the light-struck areas and which converts the reducing agent into a non-transferrable form by oxidation. The exposed layer is then brought into contact with the image-receiving layer of a material, which contains a non-photosensitive silver compound, optionally a toning agent and the reducing agents according to the invention. Both layers are then heated in contact with each other so that the reducing agent from those areas of the photosensitive layer that have not been struck by light is transferred to the image-receiving layer where it acts as additional reducing agent, which together with the phenol derivative reduces the non-photosensitive silver salt in accordance with the image. A positive image of the original is obtained. It has an obviously better blackening.

The phenol derivatives to be used according to the invention may be added to the layers in various quantities. The optimum quantity depends on the effect desired and the composition of the layer. The optimum quantity for any given case can be determined by a few simple tests well known to the average expert.

In recording materials and image-receiving materials according to the present invention the reaction partners viz. the reducing phenol derivative and the non-photosensitive silver salt are distributed non-differentially throughout the composition of a supported or self-supporting layer or are kept apart in adjacent coatings on the same support whereby they can reach each other for reacting.

In the thermographic recording material according to the present invention, e.g., an amount of the phenol derivative is used, which suffices for producing a visible blackening in the material when the latter is heated beyond 60° C.

The phenol derivatives according to the general formula are particularly suited for being used in the image-receiving material, when in this formula $R^1$ and $R^5$ are equal and each represents cyclopentyl, cyclohexyl, s-butyl or isopropyl, $R^4$ represents hydrogen, and each of $R^2$ and $R^3$ represents methyl, or each of $R^2$ and $R^4$ represents methyl and $R^3$ is hydrogen.

Fairly low concentrations of the reducing phenol derivative may be employed in the receiving material in which the non-photosensitive silver salt, e.g. a metal soap, becomes reduced at elevated temperature by the combined action of the image-wise transferred photosensitive reducing agent and that of the receiving material.

Suitable photosensitive reductors for preparing the photosensitive sheet of the two-sheet system are those that are rendered inactive and non-transferrable by heat through an exposure to short-wavelength radiation such as the pyrazolin-5-ones disclosed in U.S. Pat. No. 3,094,417 mentioned hereinbefore and German Patent No. 2,117,053 filed Apr. 7, 1971 by Agfa-Gevaert A.G., the reducing agents of the indanedione-1,3 type described in the German Patent No. 2,152,607 filed Oct. 22, 1971 by Agfa-Gevaert A.G., the acetoacetonitrile derivatives according to U.S. Pat. No. 3,619,237 mentioned hereinbefore, preferably within the scope of the following general formula:

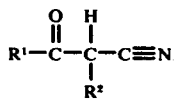

wherein:
- $R^1$ is an alkyl group, e.g. methyl, including a substituted alkyl group, an alkoxy group, an aromatic group including a substituted aromatic group, e.g. a chlorine-substituted phenyl group, or a heterocyclic group including a substituted heterocyclic group, and
- $R^2$ is an aromatic or heterocyclic group including such groups in a substituted state, e.g. a phenyl group.

The photosensitive reductor of the photosensitive copy sheet can be desensitized by exposure to ultraviolet radiation but may be rendered sensitive to radiation of longer wavelength, e.g. that from a tungsten filament lamp, by introducing a dye sensitizer in accordance with well known photochemical technology. Dye sensitizers of the erythrosin family have been found to be quite suitable but others may be used too.

According to the kind of recording system different amounts of the reducing phenol derivatives are used in the thermographic recording material or receiving material. Indeed, the optimal amount depends on the desired effect and operating conditions, and the other substances used in said materials.

Preferably at least 0.25 mole of reducing phenol derivative per mole of reducible reaction partner, viz. of the non-photosensitive silver salt, is used. Usual ratios of amounts of reducing phenol derivative to amounts of image forming oxidizing agent (substantially non-photosensitive silver salt) in a thermographic recording layer are from 0.5 to 3 moles of reducing agent to 1 mole of oxidizing agent.

In the above defined receiving material, e.g. 0.3 to 1.5 mole of reducing phenol derivative pro 1 mole of oxidizing agent (the substantially non-photosensitive silver salt) is suitable.

The reducing phenol derivatives of the present invention may be used in admixture with other reducing agents, e.g. with other known organic reducing agents in which an active hydrogen is bound to oxygen, nitrogen or carbon. They comprise, e.g. ortho-alkyl- or ortho-cycloalkyl-phenols, di- and tri-hydroxyarylaminophenols, aminonaphthols, p-phenylenediamine derivatives and hydroxylamine derivatives, gallates, alkoxynaphthols, acetoacetonitriles, pyrazolidin-3-ones, pyrazolidin-5-ones, indane-1,3-diones, hydroxytetronic acids, hydroxytetraonimides, reductones, e.g. anhydrodihydro-pyrrolidinohexosereductone, ascorbic acid derivatives, hydroxychroman derivatives, or hydroxycumarin derivatives as described, e.g., in the published German Patent Application No. 2,031,748 filed June 26, 1970 by Agfa-Gevaert A.G. In connection with reducing agents that may be used in admixture with the phenol derivatives of the above general formula particular reference is made to the published German Patent Applications Nos. 1,250,842, filed Nov. 21, 1963, 1,908,761 filed Feb. 18, 1969 both by Minnesota Mining and Manufacturing Co., 2,031,748 filed June 26, 1970, 2,235,409 filed July 19, 1972, 2,319,080 filed Apr. 16, 1973, 2,321,328 filed Apr. 27, 1973, 2,321,329 filed Apr. 27, 1973, and 2,329,144 filed June 7, 1973, all by Agfa-Gevaert A.G., and the U.S. Pat. Nos. 3,218,166, already mentioned before, and 3,653,907 of Charles H. Benbrook and Albert W. Leclair issued Apr. 4, 1972.

As has been mentioned above the reducible silver compound and reducing phenol derivative may be present in the same binder layer or in adjacent layers so that one compound, e.g. the phenol derivative, can be transferred by heat into its adjacent layer.

Particularly useful substantially non-photosensitive silver salts for being used in the materials according to the present invention are silver salts of aliphatic carboxylic acids containing a thioether group and silver salts of long-chain (at least $C_{14}$) fatty acids, e.g. silver behenate, silver palmitate, silver stearate, silver oleate, silver laurate, silver hydroxystearate, silver caprate and silver myristate.

Among these silver compounds silver behenate and silver stearate are preferred, which preferably are used together with free behenic acid and stearic acid in order to enhance the resistance to moisture of the image-receiving layer.

Other silver salts that are useful reducible substances yeilding image silver are, e.g., silver benzoate, silver phthalazinone, silver benzotriazole, silver saccharin, silver-4'-n-octadecyloxydiphenyl-4-carboxylic acid, silver o-aminobenzoate, silver acetamidobenzoate, silver camphorate, silver p-phenylbenzoate, silver phenylacetate, silver salicylate, silver butyrate, silver terephthalate, silver phthalate, silver acetate and silver hydrogen phthalate.

The image-tone of the silver image can be shifted from brown to black by the addition to the recording layer or image-receiving layer of (a) toning agent(s). Such toning agents are, e.g., 2H-phthalazinone-(1), barbituric acid, saccharin, 2-mercapto-benzoxazole phthalimides and phthalazinone derivatives e.g. 2-acyl-2H-phthalazinones, the reaction products of 2H-phthalazinone with organic isocyanates as described in the published German Patent Applications Nos. 2,220,597 and 2,220,618 both filed Apr. 27, 1972 by Agfa-Gevaert A.G. and the benz- or naphthoxazine-1,3-dione derivatives described in the published German Patent Applications Nos. 2,261,739 filed Dec. 16, 1972 and 2,328,145 filed June 2, 1973 both by Agfa-Gevaert A.G.

For the manufacture of the materials according to the invention the reducing agent and the non-photosensitive silver salt, optionally mixed with a toning agent, are preferably used together with an appropriate binder. Suitable binders are film-forming polymers, e.g. cellulose derivatives, such as cellulose ethers, cellulose esters or carboxymethylcellulose. Preferred binders are the organic polymers such as copolymers of vinyl chloride and vinyl acetate, or of butadiene and styrene, polyethylene, polyamide, polyisobutylene, polyvinyl chloride, phenol-formaldehyde resins, polyvinyl acetate, or wholly or partially saponified polyvinyl acetate, polyvinylidene chloride, polyvinylpyrrolidone, polystyrene, chlorinated rubber, polyvinylbutyral, polymers of acrylates or methacrylates, acrylamide, or copolymers of the derivatives of acrylic acid and methacrylic acid, cellulose derivatives such as cellulose acetate, cellulose propionate, or mixtures thereof, such as cellulose acetate butyrate.

The recording layer or image-receiving layer can be used in the form of a self-supporting layer though it is preferably applied to an appropriate support. The support has to be stable at processing temperatures between 60° and 200° C. Suitable supports are, e.g., sheets or foils of paper, cellulose acetate, polyethylene terephthalate, fabric, metal foils, and glass. In the case of paper supports the paper may carry the usual auxiliary layers such as baryta coatings, polyethylene coatings, etc.

The recording layer or image-receiving layer may comprise white pigments such as zinc oxide, silica, or titanium dioxide as filling agents for the improvement of the whiteness of the image background and for influencing the stickiness of the layers. Further, terpene resins and organic acids may be added to the layers for improving the keeping properties. Such layers have been described in the U.S. Pat. Nos. 3,074,809 of Richard Owen issued Jan. 22, 1963 and 3,107,174 of Thomas G. Wartman, issued Oct. 15, 1963.

In order to improve the surface structure of a thermographic copying material, which contains one of the mentioned non-photosensitive silver salts, polydimethylsiloxane compounds may be incorporated into the heat-sensitive layer such as described in Research Disclosure 1974, Item No. 11821.

The development of the thermographic copying materials containing a silver salt is performed generally at temperatures between 80° and 200° C.

The transfer of the imaging compounds from the unexposed areas of the photosensitive layers into the image-receiving layer also occurs in these range of temperatures. Heating of the materials according to the invention can be carried out, e.g. by conducting the thermographic materials or the exposed photosensitive layer in contact with the image-receiving layer over heated plates or rollers or by exposing the layer to infrared radiation. The optimum temperature and heating period depend, of course, on the imaging compound or on the composition of the non-photosensitive copying material containing the silver salt. They can be found by some simple tests.

The following examples illustrate the invention. The percentages and ratios are by weight, unless otherwise indicated.

EXAMPLE 1

An image-receiving material was prepared as follows:
0.07 kg of stearic acid were dissolved whilst stirring and heating on a water-bath at 32° C in 8 kg of ethyl acetate. To the obtained solution the following ingredients in subsequent order after dissolution of each previously added ingredient were added:

| | |
|---|---|
| modified phenol resin (acid number 18–28, melting point ASTP E 28–67 : 150° C, specific gravity at 25° C : 1.08) | 90 g |
| polyvinyl acetate (molecular weight about 1,500,000, glass transition temperature : 29° C) | 400 g |
| polyethyl methacrylate (limiting viscosity number of a 0.5% solution in chloroform at 20° C : 0.91 dl.g$^{-1}$) | 220 g |
| cellulose acetate butyrate | 80 g |

Under continued stirring the following ingredients were added:

| | |
|---|---|
| zinc oxide | 100 g |
| an amount of finely divided 2H-phthalazinone as toning agent or a toning agent of table II | |
| silver stearate | 360 g |

Whilst stirring the temperature was raised to 40° C. The homogenization was stopped after dispersion grains not larger than 5 μm were obtained.

The content of solids in the dispersion was determined and to a dispersion containing 26 g of solids per 100 ml (called Dispersion A) the following ingredients were added per 100 g of Dispersion A:

| | |
|---|---|
| 2,6-dicyclohexyl-4-methylphenol | 1.05 g |
| ethyl acetate | 120.0 g |
| methyl ethyl ketone | 20.0 g |

The content of solids of the obtained mixture was 13 g per 100 ml.

The obtained mixture was coated in a ratio of 120 ml per sq.m on a paper support and dried.

The obtained image-receiving material containing 2,6-dicyclohexyl-4-methylphenol is called image-receiving material I.

The image-receiving materials in which 2,6-dicyclohexyl-4-methylphenol has been replaced by one of the compounds 1 to 44 respectively of Table I are called image-receiving materials II to XLV.

The image-receiving materials II to XLV differ from the image-receiving material I in that the 2,6-dicyclohexyl-4-methylphenol has been replaced by an equimolar amount of one of the reducing phenol derivatives 1 to 44 of Table I.

The photosensitive copying sheet material for use in conjunction with the present receiving materials was prepared by coating onto a map overlay tracing paper the following composition at a coverage of 25 g per sq.m:

| | |
|---|---|
| 4-methoxy-1-naphthol | 1 g |
| erythrosin | 0.440 g |
| ethylcellulose | 50 g |
| methyl ethyl ketone | 500 g |

After drying, the photosensitive coating of the copying sheet was exposed in reflex to a graphic original having differential light-absorptive image and background areas. Thereafter the photosensitive copying sheet was placed with its coated face in contact with the printed text of an opaque original by means of a tungsten filament light source of 1500 W placed at a distance of 5 cm from the copying sheet for 30 s.

Thereupon the irradiated sheet was pressed with its photosensitive layer in contact at 125° C for 5 s with one of the receiving sheets as described above under the numbers I to XLV.

The resulting images on the receptor sheets II to XVI had a markedly improved colour density as compared to that of the receptor sheet I.

Table II
Toning agents

| Number of the compound | Chemical name | Molecular weight | Molecular amount |
|---|---|---|---|
| I | 5,8-dimethyl-1,3-benzoxazine-2,4-dione | 191 | $3.6 \times 10^{-3}$ mole |
| II | 7-methyl-1,3-benzoxazine-2,4-dione | 177 | $1.7 \times 10^{-3}$ mole |
| III | 2H-phthalazinone-(1) | 146 | $6.6 \times 10^{-3}$ mole |
| IV | 6,8-dimethyl-1,3-benzoxazine-2,4-dione | 191 | $3.6 \times 10^{-3}$ mole |

Table III

| Amount of reducing agent | Toning agent of Table II | Amount in the photosensitive coating | Amount in the covering layer |
|---|---|---|---|
| $3.6 \times 10^{-2}$ mole | I | $7.3 \times 10^{-3}$ mole | $7.65 \times 10^{-3}$ mole |
| | III | $2.0 \times 10^{-2}$ mole | $7.0 \times 10^{-3}$ mole |

When in the above image-receiving material I 2,6dicyclohexyl-4-methylphenol was replaced by an equimolar amount (0.8 g) of 2,6-di-t.butyl-4-methylphenol, described in the U.S. Pat. No. 3,218,166, already mentioned hereinbefore, an image with poor density (grey image-tone) and ochrous image background was obtained.

EXAMPLE 2

A mixture of the following composition is ground in a ball mill for 12 h:

| | |
|---|---|
| ethyl acetate | 40.00 g |
| stearic acid | 7.00 g |
| polymethyl methacrylate | 0.6 g |
| (the viscosity of a 5% solution in chloroform at 20° C is 0.91 cP) | |
| cellulose acetobutyrate | 0.2 g |
| (degree of substitution of acetate and | |

-continued

| | |
|---|---|
| butyrate : 0.5 and 2.4 respectively, and the viscosity of a 20% solution in acetone is 15 cP) | |
| 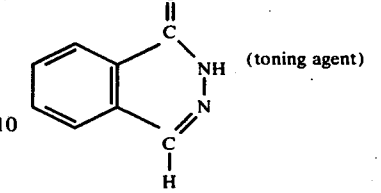 (toning agent) | 0.25 g |
| zinc oxide (average particle size : 10 μm) | 4.1 g |
| silver strearate | 0.9 g |

The following substances were then added before the mixture was applied:

| | |
|---|---|
| methyl ethyl ketone | 20.0 g |
| compound 6 of table I | $1.7 \times 10^{-4}$ mole |

The final mixture was applied to a substrated polyethylene terephthalate support in a thickness corresponding to 150 g per sq.m. After application, the layer was brought into thermally conductive contact with a paper carrying a text, which has been printed with printing ink containing carbon black, and it was then exposed to infrared radiation by contact exposure in a THERMOFAX copying apparatus, Model 47-3M.

THERMOFAX is a registered trade mark of Minnesota Mining and Manufacturing Company, St. Paul, Minn., U.S.A. for a thermographic copying apparatus.

A neutral black, positive copy with high density is obtained.

Similar good results are obtained when another compound of table I is substituted for compound 6.

We claim:

1. Thermographic recording material or image-receiving material for dry copying processes comprising at least one layer and a substantially non-photosensitive reducible silver salt, a reducing agent, and optionally a toning agent or toning mixture, wherein the reducing agent corresponds to the following general formula:

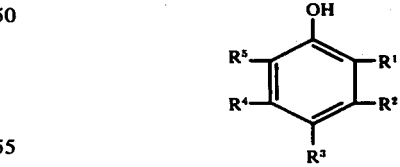

wherein:
at least one of $R^1$ and $R^5$ represents a cyclopentyl group and the other, if any, represents hydrogen,
$R^2$ represents a lower alkyl group containing 1–4 carbon atoms,
$R^3$ represents hydrogen or a lower alkyl group containing 1–4 carbon atoms, and
$R^4$ represents hydrogen.

2. Material according to claim 1, wherein the non-photosensitive silver salt and the reducing agent are present in a supported or self-supporting layer.

3. Material according to claim 1, wherein the non-photosensitive silver salt and the reducing agent are present in adjacent layers, and the reducing agent is transferrable by heat in the adjacent layer comprising the non-photosensitive silver salt.

4. Material according to claim 1, wherein the non-photosensitive silver salt is a silver salt of an aliphatic carboxylic acid containing at least 14 carbon atoms.

5. Material according to claim 1, wherein the silver salt is silver behenate or silver stearate.

6. Material according to claim 1, wherein the phenol derivative is present in an amount of at least 0.25 mole per mole of non-photosensitive silver salt.

7. Material according to claim 1, wherein a toning agent is present.

8. Material according to claim 7, wherein the toning agent is 2H-phthalazinone-(1), a phthalimide or phthalazinone derivative or a benz- or naphthoxazin-1,3-dione derivative.

9. Thermographic recording process for the production of visible silver images by image-wise heating a material comprising at least one layer and a substantially non-photosensitive silver salt and a reducing agent by exposure to infrared radiation, wherein by heating a reduction occurs of the non-photosensitive silver salt by means of a reducing agent according to the following general formula:

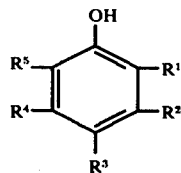

wherein:
at least one of $R^1$ and $R^5$ represents a cyclopentyl group and the other, if any, represents hydrogen,
$R^2$ represents a lower alkyl group containing 1–4 carbon atoms,
$R^3$ represents hydrogen or a lower alkyl group containing 1–4 carbon atoms, and
$R^4$ represents hydrogen.

10. Process according to claim 9, wherein a material is used comprising the non-photosensitive silver salt and the reducing agent in adjacent layers, said reducing agent being transferrable by heat in the adjacent layer containing the non-photosensitive silver salt.

11. Process according to claim 9, wherein said image-wise heating is carried out with an original containing infrared-absorbing image markings, which are brought into heat-conductive contact with the recording material.

12. Photographic recording process for the production of a visible silver image by (1) the image-wise exposure of a material comprising a layer that contains a photo-oxidizable reducing agent, which can be transferred by heat, and a photosensitive substance, which on the exposed areas transforms the reducing agent in a non-transferrable form by oxidation, (2) contacting the exposed layer with an image-receiving layer, which contains a substantially non-photosensitive silver salt, optionally a toning agent and a reducing agent, and (3) overall heating the contacting layers, the photo-oxidizable reducing agent being transferred from the non-exposed layers of the photosensitive layer into the image-receiving layer wherein the image-wise reduction of the substantially non-photosensitive silver salt takes place in the presence of a phenol derivative of the following formula:

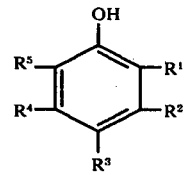

wherein:
at least one of $R^1$ and $R^5$ represents a cyclopentyl group and the other, if any, represents hydrogen,
$R^2$ represents a lower alkyl group containing 1–4 carbon atoms,
$R^3$ represents hydrogen or a lower alkyl group containing 1–4 carbon atoms, and
$R^4$ represents hydrogen.

13. Recording process according to claim 12, wherein the heating step is effected in a temperature range of 50° to 200° C.

* * * * *

UNITED STATES PATENT AND TRADEMARK OFFICE
CERTIFICATE OF CORRECTION

PATENT NO. : 4,013,473
DATED : March 22, 1977
INVENTOR(S) : Jozef Frans Willems et al It is certified that error appears in the above-identified patent and that said Letters Patent are hereby corrected as shown below:

In the Claims:

Column 18, line 21, "layers" should read -- areas --.

Signed and Sealed this

Seventeenth Day of May 1977

[SEAL]

Attest:

RUTH C. MASON
*Attesting Officer*

C. MARSHALL DANN
*Commissioner of Patents and Trademarks*